United States Patent [19]

Gruner et al.

[11] 4,403,230

[45] Sep. 6, 1983

[54] INSPECTION OF CASTINGS

[75] Inventors: Hans Gruner, Duisburg; Hans Schrewe, Düsseldorf; Lothar Parschat, Essen; Fritz-Peter Pleschiutschnigg, Duisburg, all of Fed. Rep. of Germany

[73] Assignee: Mannesmann Aktiengesellschaft, Düsseldorf, Fed. Rep. of Germany

[21] Appl. No.: 356,325

[22] Filed: Mar. 10, 1982

[30] Foreign Application Priority Data

Mar. 27, 1981 [DE] Fed. Rep. of Germany ....... 3113120

[51] Int. Cl.³ .......................... G01N 21/88; G01D 9/42
[52] U.S. Cl. ................................. 346/107 R; 250/572; 164/41
[58] Field of Search .......................... 250/572; 346/107; 358/106; 164/4.1, 150

[56] References Cited

U.S. PATENT DOCUMENTS 4,245,913 1/1981 Sarlos .............................. 250/572 X Primary Examiner—Donald A. Griffin
Attorney, Agent, or Firm—Ralf H. Siegemund

[57] ABSTRACT

A casting is inspected by equipment similar to the equipment in a companion application. That equipment includes a revolving camera. The camera is electrically powered by a generator which revolves with the camera and is, by itself, driven pursuant to that rotation.

2 Claims, 1 Drawing Figure

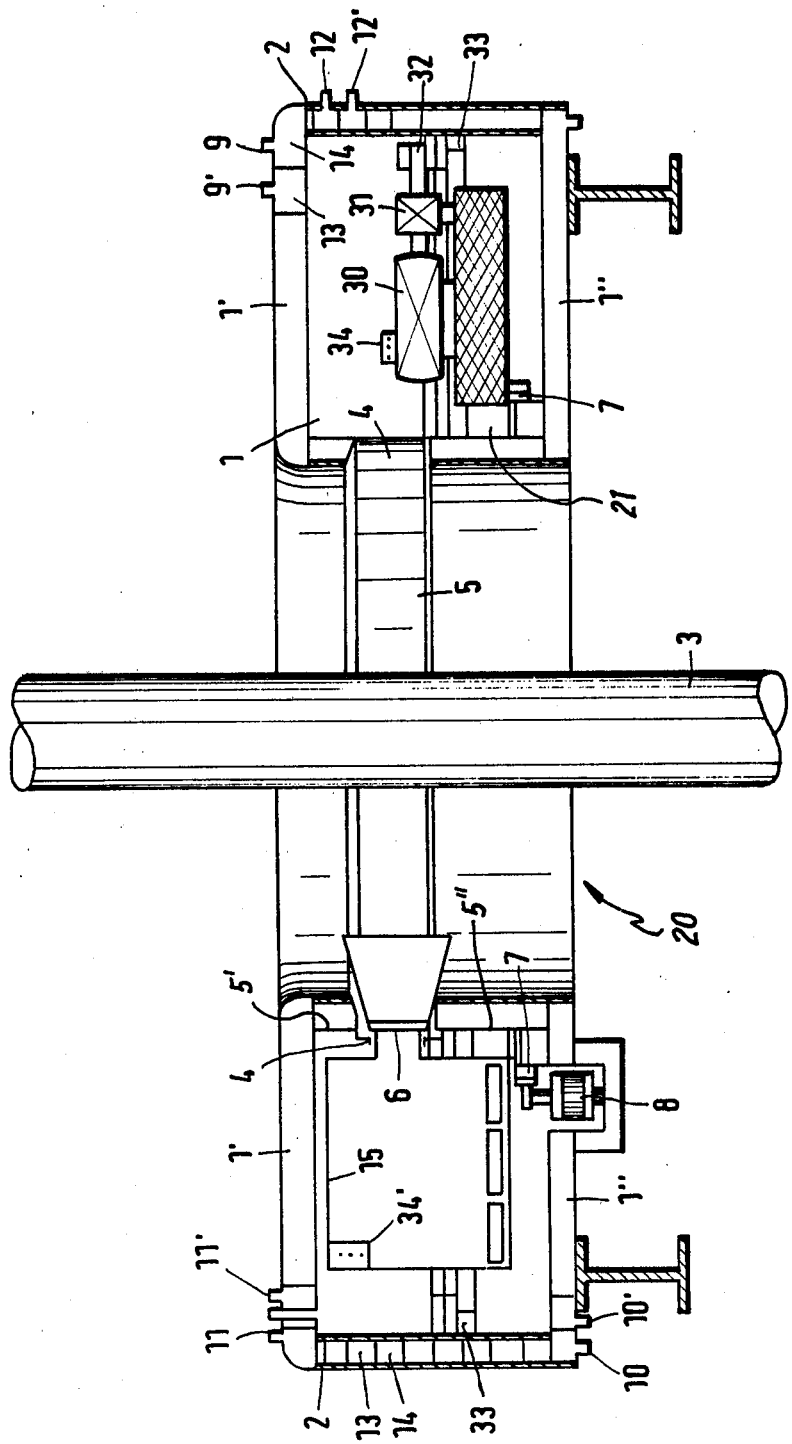

INSPECTION OF CASTINGS

BACKGROUND OF THE INVENTION

The present invention relates to the inspection of castings in a machine for continuous casting, particularly under conditions of heat emanating from the barely solidified skin of the casting.

In the past, visual inspection of a casting by experienced personnel has been common practice. The same is true with regard to solidified casting ingots; however, other inspection methods of cold ingots involve the utilization of ultrasonics, magnetic fields as they are varied by defects, chemical effects, or other metal checks. Not only does the ingot so inspected have to be cold (relatively speaking, the temperature should be lower than approximately 300° C.), but the test piece should be stationary.

German printed patent application 29 11 578 discloses a system for optical inspection of a casting, using a supplemental light source and detecting particular reflection features which can be attributed to surface defects.

In a companion patent (Application Ser. No. 337,622, filed on Jan. 7, 1982, we have proposed a device for inspecting such a casting under utilization of an annular, cooled, two-part housing having an annular, inwardly directed gap across which slides (rotates) a short sleeve, leaving but a narrow gap for a revolving detector. The detector thus rotates about the casting passing through centrally in axial direction so that a helical inspection band (hypothetical) is inscribed. This particular inspection arrangement responds specifically to the radiation that emanates from the casting and permits the early detection of surface defects. Also, the geometry of the casting can be ascertained in this manner.

DESCRIPTION OF THE INVENTION

It is an object of the present invention to improve an inspection equipment of the type set forth in our companion application identified above.

It is a particular object of the present invention to provide for a simple and reliable power supply of an inspection detector revolving about a casting that has emerged from a mold.

It is a specific object of the present invention to improve an inspection apparatus which includes an annular housing with an inward directed gap, being covered by a sheet that leaves just a narrow gap behind which a camera is located. The camera and the sheet revolve about the central axis.

In accordance with the preferred embodiment of the invention, an electric generator is mounted to revolve with the camera and the sheet as per the specific object; the generator powers the camera and another electronic equipment; an annular rack is provided in the housing and meshes a pinion which is geared to the generator. As the camera-generator-sheet subassembly revolves, the generator is driven by the pinion. The subassembly as a whole is driven by a stationary motor inside the housing. A standby battery provides electric power when the generator fails or is not driven.

DESCRIPTION OF THE DRAWINGS

While the specification concludes with claims, particularly pointing out and distinctly claiming the subject matter which is regarded as the invention, it is believed that the invention, the objects and features of the invention, and further objects, features and advantages thereof, will be better understood from the following description taken in connection with the accompanying drawings, in which:

The FIGURE illustrates an example of the preferred embodiment of the invention for practicing the best mode thereof.

Proceeding now to the detailed description of the drawings, reference numeral 20 refers to the inventive inspection equipment. It was found suitable to place it just ahead of the horizontal path of the casting as it is veered from the vertical underneath a mold into the horizontal. The station 20 is, therefore, obliquely oriented as the casting 3 is to traverse the plane of extension of station 20 at right angles. Thus, the orientation of casting 3 in the vertical, as per the figure, is for purposes of illustration only; and it is understood that the true vertical in FIG. 2 would point, e.g., into a two-o'clock position.

On the other hand, it should be noted that the preferred mode of practicing the invention is to place the inspection station as close to the mold as possible because early recognition of surface defects may permit intervention in the casting process for avoding the production of long defective castings. It is believed, at this time, that the inspection equipment can be shifted somewhat upward, but steam development of extensive external surface colling is an impediment for an optical type of inspection.

The casting 3 is surrounded by a ring-shaped housing 1, which is comprised of two parts (1' and 1") and includes a water-cooling system. Tubes 13 and 14 of rectangular cross sections run around and in the outer periphery of the housing parts to establish several cooling systems. Upper and lower housing parts do each have two cooling systems, whereby the tubes of the respective two systems are tightly interconnected and welded. In fact, these welded-together systems of tubings establish by themselves the housing parts.

The upper housing part 1' has two water inlets 9 and 9' for its two cooling systems; and there are two corresponding outlets 11 and 11' in diametrically opposed positions. The lower housing part 1" has correspondignly two inlets 12 and 12' for its two cooling systems, there being two outlets 10 and 10" accordingly. It can be seen that the two particularly identified tubes (13 and 14) pertain to different cooling systems for housing part 1".

The two housing parts are physically separated in an outer joint 2 which, however, is closed, and in an inner joint which is constructed as a rather wide annular gap 4. One can also say that the inwardly directed wall of the enclosure is provided with this annular gap 4 facing concentrically casting 3.

The annular gap 4 is closed (except, where stated below) by an annular sheet or sleeve having flange portions 5' and 5". This sheet 5 can be shifter, i.e., it may revolve about the central axis of the ring-shaped housing construction which is also the axis of the casting 3. Sheet 5 has a narrow gap 6, having its long dimension extend parallel to the direction of casting, i.e., of the movement of casting 3. A camera 15 is provided to observe and inspect the casting through that narrow gap. Camera 15 is of the diode type with a line scan.

Generally speaking, sheet 5 protects the interior of the housing from heat, water, and dirt. The sheet 5 is, in addition, provided with an annular ring gear 7; and a pinion on a shaft of a motor 8 engages that gear, causing sheet 5 and camera 15 to rotate on the central axis so that the camera is progressively oriented toward different portions of the casting 3. The particular sheet may be releasably fastened to a rotatable frame 21 which is articulated on an annular rail of the housing part 1" in a manner that permits the frame to run on this circular rail track while the camera can be swiveled up or down for proper orientation. The camera 15 is likewise affixed to that frame 21 and can be turned on the center axis of the system in order to inspect casting 3 from all sides, through the gap 6 in sheet 5. The motor 8 should be controlled toward a constant speed, selected as has been described more fully in the above-identified companion application. The drive is preferably an electric one, but a hydraulic drive or a pneumatic drive may be used instead. In either case, the drive should be stationary.

The camera and associated electronic equipment is powered by means of a voltage source 30 being also connected to the frame 21 and the annular rack 7. The power supply 30 feeds a terminal box 34, reference numeral 34' denotes the terminal box on the camera 15, there being an appropriate cable connection provided between these terminals 34 and 34'. A standby battery, not shown, may be connected in parallel to take over if, for any reason, source 30 fails or its output is reduced below the requisite level.

The source 30 may be an electric generator and rotary input for it may be derived from the rotation of the assembly 21-7-8. This is not exactly correct because source 30 itself moves; thus, strictly speaking, rotation is derived from housing 1 as the housing undergoes an apparent rotation relative to the assembly 21-7-5-15. Accordingly, a rack 33 is provided along the outer inside wall of housing 1 (portion 1") and a pinion 32 meshes this annular rack 33 in order to derive rotational motion therefrom. Pinion 32 drives a gear 31 which increases the number or revolutions and rotational speed to drive the generator 30. The components 31 and 32 revolve, of course, with frame 21, rack 7, source 30, sheet 5, and camera 15. Since motor 8 drives the entire assembly at a constant speed, the rotational motion for generator 30 is likewise constant.

The invention is not limited to the embodiments described above; but all changes and modifications thereof, not constituting departures from the spirit and scope of the invention, are intended to be included.

We claim:

1. An apparatus for inspecting the surface of a casting after having emerged from a mold in a machine for continuous casting and moving along an axis, the apparatus including a basically ring-shaped housing having an inside wall facing the casting passing centrally through the space surrounded by the ring, the wall having an annular gap; sheet means movably disposed in the housing for closing the gap, except for a small gap portion; a line scan camera in the housing connected to the sheet means and revolving therewith about said axis, the camera oriented in such a way that a narrow increment on the casting is inspected for each line scan, the improvement comprising:

an annular rack on the inside of the housing;
pinion means meshing the rack;
an electric generator mounted for revolving about axis together with said camera and said sheet means, the generator provided for powering the camera; and
means for coupling a rotational input of the generator to the pinion means so that the pinion means drives the generator as the sheet means, the camera, and the generator revolve about the housing.

2. An apparatus for inspecting the surface of a casting after having emerged from a mold in a machine for continuous casting and moving along an axis, including means defining an enclosure for surrounding the casting, and having a gap facing the casting; means for closing the gap but being capable of revolving in the enclosure so that a narrow gap in the means for closing revolves about said casting; a line scan means connected to the means for closing, revolving therewith, and observing the casting through the narrow gap, the improvement comprising:

rack means in the enclosure;
pinion means meshing the rack means;
an electric generator also connected to the means for closing and the line scan means and revolving therewith, the generator being provided for powering the line scan means; means for coupling the generator to the pinion for the pinion to drive the generator as the generator, and the line scan means revolve about said casting; and
means in the enclosure for driving the means for closing and the line scan means for obtaining said revolving, so that the pinion drives the generator.

* * * * *